(12) United States Patent
Zhao et al.

(10) Patent No.: US 8,247,064 B2
(45) Date of Patent: Aug. 21, 2012

(54) COATINGS

(75) Inventors: Qi Zhao, Scotland (GB); Eric Abel, Scotland (GB)

(73) Assignee: The University Court of the University of Dundee (GB)

( * ) Notice: Subject to any disclaimer, the term of this patent is extended or adjusted under 35 U.S.C. 154(b) by 1082 days.

(21) Appl. No.: 10/524,755

(22) PCT Filed: Jul. 10, 2003

(86) PCT No.: PCT/GB03/03007
§ 371 (c)(1),
(2), (4) Date: Sep. 7, 2005

(87) PCT Pub. No.: WO2004/006977
PCT Pub. Date: Jan. 22, 2004

(65) Prior Publication Data
US 2006/0150862 A1    Jul. 13, 2006

(30) Foreign Application Priority Data
Jul. 10, 2002    (GB) .................................. 0215916.8

(51) Int. Cl.
*B32B 7/00* (2006.01)
*A61F 2/02* (2006.01)
*A61F 2/28* (2006.01)

(52) U.S. Cl. ........ 428/212; 428/408; 623/1.1; 623/1.49; 623/4.1; 623/6.56; 623/6.57; 623/11.11; 623/23.7; 623/32.71

(58) Field of Classification Search .................. None
See application file for complete search history.

(56) References Cited

U.S. PATENT DOCUMENTS

| | | |
|---|---|---|
| 5,725,573 A | 3/1998 | Dearnaley et al. |
| 5,945,153 A | 8/1999 | Dearnaley |

FOREIGN PATENT DOCUMENTS

| | | |
|---|---|---|
| DE | 4219636 A1 | 12/1993 |
| DE | 20020649 U1 | 5/2002 |
| EP | 0514586 B1 | 11/1992 |
| GB | 1344681 | 1/1974 |
| GB | 2287473 A | 9/1995 |
| JP | 05163582 A | 6/1993 |
| WO | WO 00/47402 A1 | 8/2000 |
| WO | WO 00/75394 A1 | 12/2000 |
| WO | WO 01/43790 A2 | 6/2001 |
| WO | WO 01/43790 A3 | 6/2001 |
| WO | WO 01/97718 A1 | 12/2001 |

OTHER PUBLICATIONS

International Search Report corresponding to PCT/GB03/003007 mailed on Jan. 23, 2004.

Sharma, P.K., et al., "Analysis of different approaches for evaluation of surface energy of microbial cells by contact angle goniometry", *Advances in Colloid and Interface Science*, 98:341-463 (2002).

(Continued)

*Primary Examiner* — Vivian Chen
(74) *Attorney, Agent, or Firm* — Myers Bigel Sibley & Sajovec, PA

(57) ABSTRACT

This invention relates to coating a surface wherein the coated surface inhibits foulants such as cell and/or protein and/or prion adhesion or formation. In particular, the coated surface may be part of a medical device which inhibits bacterial adhesion and colonisation, thrombus formation and/or prion, blood protein and/or protein formation.

10 Claims, 2 Drawing Sheets

OTHER PUBLICATIONS van Oss, C.J., et al., "Acid-base interfacial interactions in aqueous media", *Colloids and Surfaces A; Physiochemical and Engineering Aspects*, 78:1-49 (1993).

Zhao Q., et al., "Effect of temperature on the surface free energy of amorphous carbon films", *Journal of Colloid and Interface Science*, 280:174-183 (2004).

Examination Report corresponding to European Patent Application No, 03740788.9 dated Oct. 19, 2005.

Examination Report corresponding to European Patent Application No. 03740788.9 dated Oct. 8, 2009.

Examination Report corresponding to European Patent Application No. 03740788.9 dated Mar. 3, 2010.

Examination Report corresponding to European Patent Application No. 03740788.9 dated Apr. 7, 2010.

Response to EPO corresponding to European Patent Application No. 03740788.9 dated Feb. 16, 2010.

Response to EPO corresponding to European Patent Application No. 03740788.9 dated Mar. 5, 2010.

COATINGS

RELATED APPLICATIONS

This application claims priority under 35 U.S.C. §371 from PCT Application No. PCT/GB03/003007, filed in English on Jul. 10, 2003, which claims the benefit of Great Britain Application Ser. No. 0215916.8 filed on Jul. 10, 2002, the disclosures and contents of which are incorporated by reference herein in their entireties.

FIELD OF THE INVENTION

This invention relates to coating a surface wherein the coated surface inhibits foulants such as cell and/or protein and/or prion adhesion or formation. In particular, the coated surface may be part of a medical device which inhibits bacterial adhesion and colonization, thrombus formation and/or prion, blood protein and/or other protein formation.

BACKGROUND OF THE INVENTION

A problem which exists in the art is that implanted medical devices are prone to bacterial adhesion and colonization on their surface. Implanted medical devices are also susceptible to thrombus formation and prion, blood protein and/or other protein formation.

Infections arising from the use of implanted medical devices, such as heart valves, stents, catheters, joint prostheses, intraocular lenses and dental implants etc. are associated with increased morbidity and mortality, prolonged hospitalisation, patient discomfort and increased medical costs. Progress in the area of anti-microbial treatment has been of limited success. For example, infection reportedly occurs in up to 13.9% of patients following stabilization of open fractures and in about 2% of patients who receive joint prostheses. Due to infection, prosthetic valve endocarditis remains one of the most dangerous and life-threatening complications following heart valve replacement. Mortality rates as high as 75% have been reported. Furthermore, urinary or vascular catheters are associated with a high rate of infection, about 7.6 infections per 1000 catheter-days.

Anti-microbial coatings for medical devices have recently emerged as a potentially effective method for preventing device-related infections. This is achieved by releasing anti-microbial agents from a coating to kill bacteria or to inhibit bacterial colonization. Some medical devices such as prosthetic heart valve sewing rings, stents, catheters and orthopaedic implants coated with anti-microbial agents have been reported. The anti-microbial agents used are silver, antibiotics combined with minocycline and rifampin, and surfactants etc. (Haley R W, "Estimating the Extra Charges and Prolongation of Hospitalisation Due to Nosocomial Infections: A Comparison of Methods". J. Infect. Dis., 141:248-257 (1980); DiTizio V, Ferguson G W, Mittelman M W, Khoury A E, Bruce A W, DiCosmo F, "A Liposomal Hydrogel for the Prevention of Bacterial Adhesion to Catheters", Biomaterials, 19:20, 1877-1884 (1998); Illingworth B L, Tweden K, Schroeder R E, Cameron J D, "In Vivo Efficacy of Silver-Coated (Silzone (TM)) Infection-Resistant Polyester Fabric Against a Biofilm-Producing Bacteria, *Staphylococcus* Epidermidis", Journal Of Heart Valve Disease, 7: (5) 524-530 (1998); Stamm W E. "Catheter-Associated Urinary Tract Infections: Epidemiology, Pathogenesis, and Prevention", Am. J. Med., 91:65-71 (1991); Darouiche, R O, "Prevention of Vascular Catheter-Related Infections", The Netherlands Journal of Medicine 55:92-99 (1999)).

However, the currently available antimicrobial coatings have the problems of poor abrasion and poor corrosion resistance, limited biocompatibility and other adverse side effects. For example, the local cytotoxicity of silver-coated catheter cuffs and orthopaedic implants on human fibroblast cells has been observed.

Furthermore, there has been a growing understanding that the generation of wear debris due to friction at articulating surfaces or the release of metal ions can lead to severe cell response and bone resorption or osteolysis, giving rise to premature failure of implants.

Blood contacting devices often suffer from thrombus formation due to limited haemocompatibility. The interaction of an implanted material surface with blood stimulates platelet activation, leading to blood coagulation and thrombus formation. Numerous studies have been done to reduce thrombus formation by coating device surfaces with diamond-like carbon or bioactive materials. Diamond-like carbon shows great promise as a durable, wear- and corrosion-resistant coating for biomedical implants. Despite these favourable results and continuous technical improvements, the application of stents, artificial arteries and vascular catheters etc. is still limited by subacute occlusion and restenosis due to thrombus formation, especially in low flow and stagnation zones. The initial step of thrombus formation on blood-contacting biomaterials is known to be adsorption of blood proteins followed by platelet adhesion. However, diamond-like carbon coatings cannot inhibit blood protein adhesion to their surfaces significantly.

Cleaning, disinfection and sterilization of surgical instruments is crucial as they are in direct contact with blood and internal organs. It is critical that prior to any disinfection or sterilisation procedure that all items undergo a thorough physical cleaning. However, the stains on the surfaces of surgical devices from contamination are not easily removed. Prion (a microscopic protein particle similar to a virus but lacking nucleic acid, thought to be the infectious agent responsible for scrapie and certain other degenerative diseases of the nervous system) diseases constitute a unique infection control problem because prions exhibit unusual resistance to conventional chemical and physical decontamination methods. Recommendations to prevent cross-transmission of infection from medical devices contaminated by Creutzfeldt-Jakob disease (CJD) have been based primarily on prion inactivation studies. On the basis of the scientific data, only critical (e.g. surgical instruments) and semicritical devices contaminated with high-risk tissue (i.e. brain, spinal cord and eye tissue) from high-risk patients—those with known or suspected infection with CJD—require special treatment. The whole issue of contamination has become highly topical recently with concerns about the spread of CJD through surgical and butchers' instruments (e.g. knives). So far no attempts have been made to develop CJD-resistant surgical instruments.

It is an object of at least one aspect of the present invention to obviate/mitigate one or more of the aforementioned disadvantages.

It is a further object of the present invention to provide coatings with anti-microbial properties and/or improved haemocompatibility.

It is yet a further object of the present invention to provide a material which may be coated on a surface or substrate which is capable of inhibiting any of the following from adhering to surfaces: microorganisms, platelets, proteins (blood protein or prion protein) and/or cells.

SUMMARY OF THE INVENTION

According to a first aspect of the present invention there is provided a modified surface wherein the adhesion or attachment of particles to the modified surface has been minimised or prevented by adjusting the Lifshitz-van der Waals (LW) surface free energy of an unmodified surface to be equal to or approximately equal to the Lifshitz-van der Waals (LW) surface free energy of particles in an environment surrounding the surface when the modified surface is in use.

The particles may be foulants.

The particles may be selected from any of the following: cells, proteins, prions, bacteria, amino acids, nucleic acids, metallic based compounds, organometallics, organic compounds, inorganic compounds or any other type of discrete separate particles.

Typically, there is a surface with a Lifshitz-van der Waals (LW) surface free energy of $\gamma^{LW}_{Surface}$ on which the adhesion or attachment of particles is minimised or prevented by modifying the surface free energy $\gamma^{LW}_{Surface}$ of the surface in accordance with the Lifshitz-van der Waals (LW) surface free energy of the particles so that:

$$\gamma^{LW}_{surface} \cong \gamma^{LW}_{S,Min}$$

wherein $\gamma^{LW}_{S,min}$ is the minimum level of attachment to a surface S and is defined as follows:

$$\sqrt{\gamma^{LW}_{S,Min}} = (\tfrac{1}{2})(\sqrt{\gamma^{LW}_{particles}} + \sqrt{\gamma^{LW}_{environment}})$$

where $\gamma^{LW}_{particles}$ is the LW surface free energy of particles, and $\gamma^{LW}_{environment}$ is the LW surface free energy of an environment when the modified surface is in use.

In one example, the surface may be one which comes into contact with cells and/or proteins and/or prions within a living human or animal body. In this example there is a surface with a Lifshitz-van der Waals (LW) surface free energy of $\gamma^{LW}_{Surface}$ on which the adhesion or attachment of cells and/or proteins and/or prions is minimised or prevented by modifying the surface free energy $\gamma^{LW}_{Surface}$ of the surface in accordance with the Lifshitz-van der Waals (LW) surface free energy of the cells and/or proteins and/or prions so that:

$$\gamma^{LW}_{surface} \cong \gamma^{LW}_{S,Min}$$

wherein $\gamma^{LW}_{S,min}$ is the minimum level of attachment to a surface S and is defined as follows:

$$\sqrt{\gamma^{LW}_{S,Min}} = (\tfrac{1}{2})(\sqrt{\gamma^{LW}_{cells and/or proteins and/or prions}} + \sqrt{\gamma^{LW}_{solution and/or whole blood}})$$

where $\gamma^{LW}_{cells and/or proteins and/or prions}$ is the LW surface free energy of cells and/or proteins and/or prions, and $\gamma^{LW}_{solution and/or whole blood}$ is the LW surface free energy of a solution and/or of whole blood.

Conveniently, the surface is modified with a coating of modified diamond-like carbon (DLC), Ag—PTFE-surfactant or Ni—Cu—P—PTFE wherein the coated surface inhibits bacterial adhesion and colonisation, thrombus adhesion to the surface and foulant formation (i.e. particle formation) such as prion, blood protein and/or other protein formation.

Typically, the diamond-like carbon (DLC) is modified by incorporating elements selected from any of the following: halogens such as fluorine, chlorine and bromine; Group IV elements such as silicon and germanium; Group V elements such as nitrogen and phosphorous; Group VI elements such as oxygen and sulphur; and transition metals such as titanium, tantalum, tungsten and niobium. The elements may be present in an amount of 0-40% by weight. The elements may be incorporated into the diamond-like carbon by co-sputtering.

Alternatively, the elements are incorporated into the diamond-like carbon (DLC) using reactive gases such as fluorinous monomers (e.g. $C_2F_2$, $C_2F_4$ and $HCF_3$), silicon organic monomers (e.g. $Si(CH_3)_4$) gaseous hydrocarbons (eg. $C_2H_2$) and gases such as $O_2$ and $N_2$.

The modified diamond-like carbon (DLC) may be deposited using any of the following methods: microwave plasma deposition, plasma-enhanced vapour deposition, plasma-induced cold deposition, magnetron sputtering and ion beam-assisted deposition.

The surfactant in the Ag—PTFE-surfactant may be non-ionic, anionic or cationic.

Typically, the ratio of Ag:PTFE:surfactant is about 80-60%:10-39%:1-10% by weight and preferably 75%:22%:3% by weight.

Preferably, the surfactant in the Ag—PTFE-surfactant is selected from any of the following: $C_{20}H_{20}F_{23}N_2O_4I$, and polyoxyethylene nonylphenyl ether.

The polyoxyethylene nonylphenyl ether may be selected from any of the following:

4-$(C_9H_{19})C_6H_4(OCH_2CH_2)_nOH$, n≈12, Hydrophile Lipophile Balance (HLB)=12; 4-$(C_9H_{19})C_6H_4(OCH_2CH_2)_nOH$, n≈40, HLB=17.8; 4-$(C_9H_{19})C_6H_4(OCH_2CH_2)_nOH$, n≈100, HLB=19; and $(C_9H_{19})_2C_6H_3(OCH_2CH_2)_nOH$, n≈150, HLB=19.

Typically, the Ag—PTFE-surfactant coating is obtained using an electroless plating technique.

Alternatively, the Ag—PTFE-surfactant coating is obtained using an electroless plating technique.

Typically, the Ni—Cu—P—PTFE coating is obtained using an electroless plating technique.

Alternatively, the Ni—Cu—P—PTFE coating is obtained using an electroplating technique.

Typically, the ratio of Ni:Cu:P:PTFE is about 97-40%:1-20%:1-20%:1-20% by weight. In one particular example, for inside a body the Ni:Cu:P:PTFE ratio may be 80%:11%:4%:5% by weight. It should be realised that for inside different bodies a different ratio may be required due to slightly different environments.

Conveniently, the surface which is coated is selected from any of the following: healthcare products; dental care products; baby care products; personal hygiene products; consumer cleaning and disinfectant products; institutional and industrial cleaning products; food preparation devices and packaging; water storage products; water treatment products; water delivery systems; biofilm sensitive systems; and laboratory and scientific equipment.

The coated surface may be part of a medical device. In particular, the medical device may be selected from any of the following: endoscopes and accessories; ophthalmic equipment; dental equipment; surgical instruments; heart valves; stents; catheters; joint prostheses; intraocular lenses, dental implants, electrodes and cable equipment.

The coated surface may inhibit the following bacteria: *Staphylococcus epidermidis, Staphylococcus aureus, Pseudomonas aeruginosa, Escherichia coli, Candida albicans* or any other microorganisms which could cause device-related infections.

According to a second aspect of the present invention there is provided a method for preventing or minimising the adhesion or attachment of particles to a surface by modifying the surface to form a modified surface so that the Lifshitz-van der Waals (LW) surface free energy of the modified surface is equal to or approximately equal to the Lifshitz-van-der Waals (LW) surface free energy of particles in an environment surrounding the surface.

According to a third aspect of the present invention there is provided a device comprising a modified surface wherein the modified surface prevents or minimises the attachment of particles to the modified surface.

Typically, the device is a medical device. In particular, the medical device may be selected from any of the following: endoscopes and accessories; ophthalmic equipment; dental equipment; surgical instruments; heart valves; stents; catheters; joint prostheses; intraocular lenses; dental implants; electrodes and cable equipment.

According to a fourth aspect of the present invention there is provided a method of modifying a surface wherein the surface is modified so that the adhesion or attachment of particles to the modified surface has been minimised or prevented by adjusting the Lifshitz-van der Waals (LW) surface free energy of an unmodified surface to be equal to or approximately equal to the Lifshitz-van der Waals (LW) surface free energy of particles in an environment surrounding the surface when the modified surface is in use.

According to a fifth aspect of the present invention there is provided use of a device comprising a modified surface according to the first aspect wherein the modified surface prevents or minimises the attachment of particles to the modified surface.

BRIEF DESCRIPTION OF THE DRAWINGS

Embodiments of the present invention will now be described, by way of example only, with reference to the accompanying drawings in which.

DETAILED DESCRIPTION OF THE INVENTION

Figure 1:
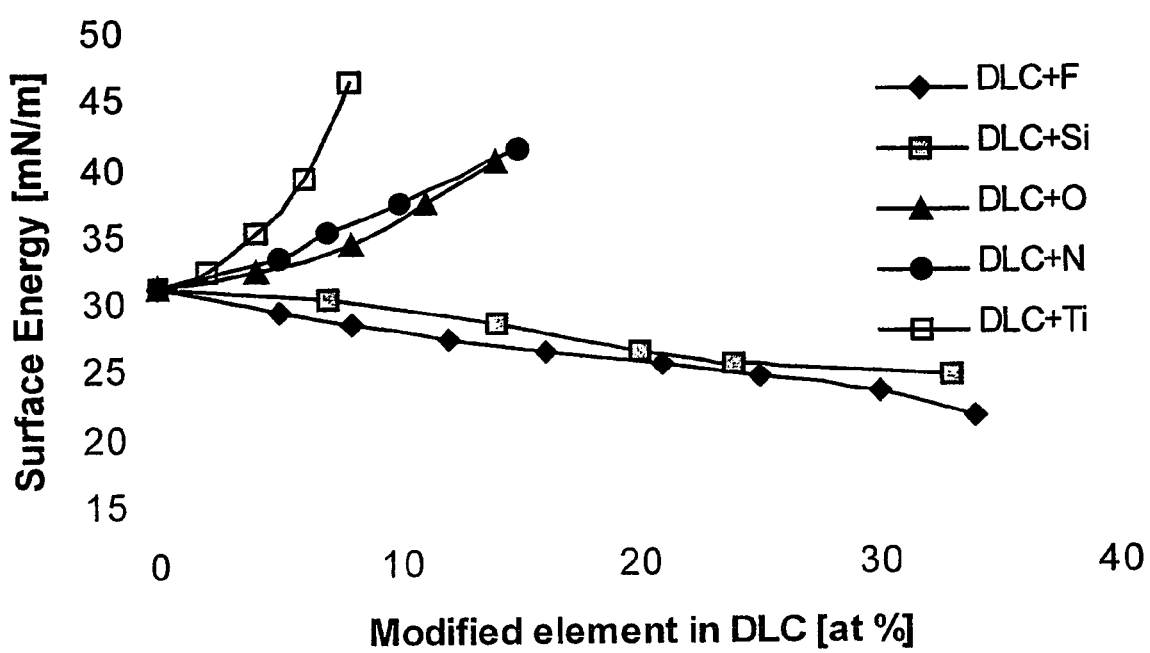
FIG. 1 is a graph showing the surface free energy for a variety of diamond-like carbon (DLC) coatings.

The first theory used to explain interactions involving colloidal particles or bacterial adhesion was the DLVO theory, named after four scientists, Deryagin, Landau, Verwey and Overbeek. According to the DLVO theory, the principal interaction forces determining hetero-coagulation include a Lifshitz-van der Waals (LW) interaction component, an electrostatic double-layer component (EL), a Lewis acid-base component (AB), and a Brownian motion component (Br). The theory involves several complex equations and has been used as a qualitative model (Bos R, Busscher H J, Role of Acid-Base Interactions on the Adhesion of Oral Streptococci and Actinomyces to Hexadecane and Chloroform—Influence of Divalent Cations and Comparison Between Free Energies of Partitioning and Free Energies Obtained by Extended DLVO Analysis, Colloids And Surfaces B-Biointerfaces, Vol. 14, pp. 169-177(1999)).

In the present application the DLVO theory has been extended. The extended DLVO theory showed that the adhesion or attachment of particles such as cells and/or proteins and/or prions to a surface is minimised or prevented if the Lifshitz-van der Waals (LW) surface free energy of the surface, $\gamma^{LW}_{surface}$ is modified so that it is equal or approximately equal to $\gamma^{LW}_{s,min}$ as defined below:

$$\sqrt{\gamma^{LW}_{S,Min}} = (1/2)(\sqrt{\gamma^{LW}_{particles}} + \sqrt{\gamma^{LW}_{environment}})$$

where $\gamma^{LW}_{particles}$ is the LW surface free energy of particles and $\gamma^{LW}_{environment}$ is the surface free energy of the environment.

In one example and for inside a particular human or animal body the Lifshitz-van der Waals (LW) surface free energy may be defined as follows:

$$\sqrt{\gamma^{LW}_{S,Min}} = (1/2)(\sqrt{\gamma^{LW}_{cells and/or proteins and/or prions}} + \sqrt{\gamma^{LW}_{solution and/or whole blood}})$$

where $\gamma^{LW}_{cells\ and/or\ proteins\ and/or\ prions}$ is the LW surface free energy of cells and/or proteins and/or prions and $\gamma^{LW}_{solution\ and\ or\ whole\ blood}$ is the LW surface free energy of a solution and/or of whole blood. It should be realised that inside different bodies and inside different areas of the body there will be different surface free energies.

Based on this theoretical model, it was derived that the time required to form a mono-layer of particles such as cells and/or proteins and/or prions on a surface is as follows:

$$\text{time} = f(C/|\sqrt{\gamma^{LW}_{Surface}} - \sqrt{\gamma^{LW}_{S,min}}|)$$

where C is constant which is dependant on the properties of attached particles. The equation indicates that if the LW surface free energy, $\gamma^{LW}_{surface}$, is equal to $\gamma^{LW}_{S,min}$ (i.e. $\gamma^{LW}_{surface} \equiv \gamma^{LW}_{s,min}$), the time required to form a mono-layer of particles such as cells and/or proteins and/or prions on a surface is infinite.

In general, the LW surface free energy of, for example, a medical device is unlikely to be equal to $\gamma^{LW}_{S,min}$. The end result is that the LW surface free energy of devices therefore have to be altered by a surface modification technique, so that $\gamma^{LW}_{Surface} \equiv \gamma^{LW}_{S,min}$.

The present invention relates to three different types of coating: modified diamond-like carbon coatings, Ag—PTFE-surfactant coatings and Ni—Cu—P—PTFE nano-composite coatings.

By modifying diamond-like carbon the interaction forces between a modified diamond-like carbon surface and cells and/or proteins and/or prions may be altered so as to prevent bacterial adhesion and colonization, thrombus formation and inhibit prion, blood protein and/or other protein formation. This may be predicted using the above-mentioned equations.

The diamond-like carbon is modified by incorporating elements selected from any of the following: halogens such as fluorine, chlorine and bromine; Group IV elements such as silicon and germanium; Group V elements such as nitrogen and phosphorous; Group VI elements such as oxygen and sulphur; and transition metals such as titanium, tantalum, tungsten and niobium. The incorporated elements are present in an amount of 0-40% by weight and are chemically and/or physically bonded to the diamond-like carbon.

The elements are incorporated into the diamond-like carbon by co-sputtering or by adding reactive gases such as fluorinous monomers (e.g. $C_2F_2$, $C_2F_4$, $HCF_3$), silicon organic monomers (e.g. $Si(CH_3)_4$) gaseous hydrocarbons (e.g. $C_2H_2$) and gases such as $O_2$ and $N_2$ to the working gas during the coating process. The working gas is for example, argon. A variety of deposition methods may be used including microwave plasma deposition, plasma-enhanced vapour deposition, plasma-induced cold deposition, magnetron sputtering and ion beam-assisted deposition etc.

A plasma enhanced (or activated) chemical vapour deposition process is described as follows. Diamond-like carbon coatings may be modified by the deposition of elements (e.g. fluorinous monomers (e.g. $C_2F_2$, $C_2F_4$ and $HCF_3$); silicon organic monomers (e.g. $Si(CH_3)_4$,) gaseous hydrocarbons (e.g. $C_2H_2$) and gases such as $O_2$ and $N_2$ in a plasma enhanced (or activated) chemical vapour deposition process. The deposition system mainly consists of a tube reactor with a radio frequency (rf) generator, a power electrode, a self-bias device and a turbo pump. A typical power density during the deposition is about 0.1-0.8 W/cm$^2$ with negative self-bias of about 400-1800 V. The gas flow rate is about 10~150 cm$^3$/min. The gas ratio (e.g. $C_2F_4$:$C_2H_2$ or $HCF_3$:$C_2H_2$) is about 0~25. Before deposition, the samples need cleaning by argon etching.

A combined radio frequency (rf) plasma and magnetron sputtering technique is described as follows. Modified diamond-like carbon coatings containing the required elements (e.g. Ti, O, F etc.) may be produced using a combined radio frequency (rf) plasma and magnetron sputtering process from a mixture (e.g. acetylene and $Ti(C_2H_5O)_4$) in a high vacuum system with a base pressure of more than $2 \times 10^6$ Pa. The coatings may be deposited on various substrates, such as stainless steel. The rf generator output may be regulated to yield a constant sample self-bias of about −400~−600 V. Sample substrates are cleaned ultrasonically in a 1:1 ratio of acetone/ethanol prior to film deposition. After plasma cleaning for 2 mins at 3 Pa argon pressure, the depositions are performed with a total mixture pressure of 2 Pa. Adjusting DC sputter power between 30 and 200 V and the element ratio in the mixture, enables deposited films with different element (e.g. Ti, O, F etc) concentrations ranging from 1 to 25% by weight. The substrate temperature during deposition is about 150° C.

Ion beam-assisted deposition (IBAD) is a vacuum deposition process that combines physical vapour deposition (PVD) with ion beam bombardment. A vapour of coating atoms is generated with an electron beam evaporator and deposited on a substrate. Ions, typically gaseous species, are simultaneously extracted from a plasma and accelerated into a growing PVD film at energies of several hundred to several thousand electron Volts. The ions interact with coating atoms, driving them into the substrate and producing a graded material interface, which enhances adhesion. The major processing parameters are shown in the Table below:

| | |
|---|---|
| Base pressure | 7~9 × 10$^4$ Pa |
| Ar$^+$ sputtering ion energy | 1~5 keV |
| Ar$^+$ sputtering ion current | 30~70 mA |
| Hydrocarbon bombarding ion energy | 200~1000 eV |
| Hydrocarbon bombarding ion current | 8~15 mA |
| Deposition temperature | <80° C. |

FIG. 1 shows that the surface energy of diamond-like carbon coatings may be adjusted over a wide range in a well-controlled manner by the incorporation of elements such as F, Si, O, N or Ti into the surface. This means that the surface energy of modified diamond-like carbon coatings can be adjusted to a required value. Cells and/or proteins and/or prions may therefore be inhibited from attachment or adhesion.

The modified diamond-like carbon is found to have improved mechanical stability over normal diamond-like carbon.

A Ag—PTFE-surfactant coating is also used as an antibacterial coating. The incorporation of PTFE and a surfactant into a metal matrix takes advantage of different properties of the metal, the PTFE and the surfactant. The ratio of Ag:PTFE:surfactant is about 80-60%:10-39%:1-10% by weight and is preferably 75%:22%:3% by weight.

Suitable surfactants are selected from a $C_{20}H_{20}F_{23}N_2O_4I$ compound or a polyoxyethylene nonylphenyl ether. The polyoxyethylene nonylphenyl ether is selected from any of the following:

4-$(C_9H_{19})C_6H_4(OCH_2CH_2)_n$OH, n≈12, Hydrophile Lipophile Balance (HLB)=12; 4-$(C_9H_{19})C_6H_4(OCH_2CH_2)_n$OH, n≈40, HLB=17.8; 4-$(C_9H_{19})C_6H_4(OCH_2CH_2)_n$OH, n≈100, HLB=19; and $(C_9H_{19})_2C_6H_3(OCH_2CH_2)_n$OH, n≈150, HLB=19.

The Ag—PTFE-surfactant coating is obtained using an electroless plating technique which merely comprises immersing the device or part of the device to be coated. A thickness of about 2-5 micrometres is obtained.

The third type of coating is Ni—Cu—P—PTFE which is obtained via a similar electroless plating technique to the Ag—PTFE-surfactant coating. The ratio of the different constituents is selected in order to obtain the value of $\gamma^{LW}_{s,min}$. For various particles their $\gamma^{LW}_{s,min}$ values may be different, so the ratio of the constituents may be different.

Products which are coated using modified diamond-like carbon coatings, Ag—PTFE-surfactant coatings and Ni—Cu—P—PTFE nanocomposite coatings may be selected from any of the following: healthcare products; dental care products; baby care products; personal hygiene products; consumer cleaning and disinfectant products; institutional and industrial cleaning products; food preparation devices and packaging; water storage and water treatment products and delivery systems; biofilm sensitive systems; and laboratory and scientific equipment.

In particular, medical devices selected from any of the following may be coated: endoscopes and accessories; opthalmic equipment; dental equipment; and surgical instruments; heart valves; stents; catheters; joint prostheses; intravascular lenses and dental implants.

EXAMPLES

Comparative Example 1

Figure 2:
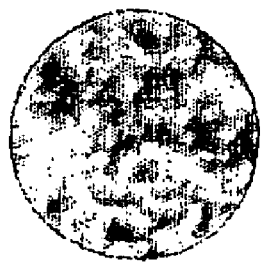
FIG. 2 is a microscope image of the amount of bacteria on a diamond-like carbon (DLC) coated surface according to the prior art.

FIG. 2 is a microscope image of the amount of bacteria found on a surface of a medical device with a diamond-like carbon coating (i.e. unmodified). There is a bacteria density of 602000 cells/cm$^2$.

Example 1

Figure 3:
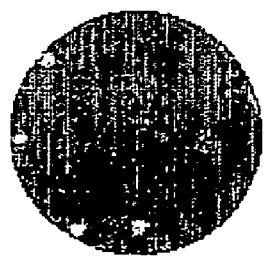
FIG. 3 is a microscope image of the amount of bacteria on a modified diamond-like carbon (DLC) coated surface comprising fluorine according to a first embodiment of the present invention.

FIG. 3 is a microscope image of the amount of bacteria found on a surface of a medical device with a coating of modified diamond-like carbon which comprises about 4% fluorine. There is a bacteria density of 407 cells/cm$^2$. A combined radio frequency (rf) plasma and magnetron sputtering technique is used to form the coating which is about 2 micrometers thick.

Example 2

Figure 4:
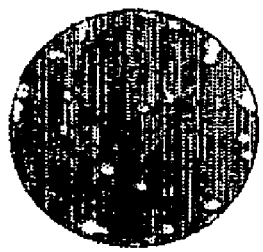
FIG. 4 is a microscope image of the amount of bacteria on a Ag—PTFE-$C_{20}H_{20}F_{23}N_2O_4I$ surfactant coated surface according to a second embodiment of the present invention.

FIG. 4 is a microscope image of the amount of bacteria found on a surface of a medical device with a Ag—PTFE-$C_{20}H_{20}F_{23}N_2O_4$ surfactant coating of about 4 micrometers thick. The ratio of Ag:PTFE:surfactant is 75%:22%:3% by weight. There is a bacteria density of 614 cells/cm$^2$.

To form this coating the following electroless plating technique is used:

| Procedures | Conditions |
| --- | --- |
| 1. Alkaline cleaning | NaOH: 20~30 g/l; Na$_2$CO$_3$: 25~30 g/l; Na$_3$PO$_4$: 25~35 g/l; Na$_2$SiO$_3$: 5~10 g/l; Temperature: 60~80° C., Time: 5~10 min. |
| 2. Rinsing | With water. Room temperature. |
| 3. Cathodic electrocleaning | NaOH: 25~35 g/l; Na$_2$CO$_3$: 25~30 g/l; Na$_3$PO$_4$: 25~35 g/l; Na$_2$SiO$_3$: 5~10 g/l; voltage: 5~7 V; Room temperature; Time: 2~3 min. |
| 4. Rinsing | With water. Room temperature. |
| 5. Pickling | HCl (30%): H$_2$O = 1:1; Room temperature. Time: 0.5~1 min. |
| 6. Activation (to coat a super-thin layer Ni) | NiCl$_2$.6H$_2$O: 200~400 g/l; HCl (30%): 75~200 ml/litre; Anode plates: Ni; Cathodic current: 2~3 A/dm$^2$; Room temperature; Time: 1 min. |
| 7. Electroless plating Ni—P | NiCl$_2$.6H$_2$O: 20~30 g/l; Na$_3$C$_6$H$_5$O$_7$.6H$_2$O: 15~30 g/l; NaH$_2$PO$_2$: 15~35 g/l; C$_3$H$_6$O$_3$: 20~30 g/l; Temperature: 85~90° C.; pH: 4.6~5.0 |
| 8. Rinsing | With water. Room temperature. |
| 9. Electroless plating with Ag-PTFE surfactant | 30~90° C., pH: 4.8~9.0 |
| 10. Rinsing | With water. Room temperature. |

Example 3

The following electroless plating technique is used to form a coating of Ni—Cu—P—PTFE nano-composite. The ratio of Ni:Cu:P:PTFE is 80%:11%:4%:5% by weight.

| Procedures | Conditions |
| --- | --- |
| 1. Alkaline cleaning | NaOH: 20~30 g/l; Na$_2$CO$_3$: 25~30 g/l; Na$_3$PO$_4$: 25~35 g/l; Na$_2$SiO$_3$: 5~10 g/l; Temperature: 60~80° C., Time: 5~10 min. |
| 2. Rinsing | With water. Room temperature. |
| 3. Cathodic electrocleaning | NaOH: 25~35 g/l; Na$_2$CO$_3$: 25~30 g/l; Na$_3$PO$_4$: 25~35 g/l; Na$_2$SiO$_3$: 5~10 g/l; voltage: 5~7 V; Room temperature; Time: 2~3 min. |
| 4. Rinsing | With water. Room temperature. |
| 5. Pickling | HCl (30%): H$_2$O = 1:1; Room temperature. Time: 0.5~1 min. |
| 6. Activation (to coat a super-thin layer Ni) | NiCl$_2$.6H$_2$O: 200~400 g/l; HCl (30%): 75~200 ml/litre; Anode plates: Ni; Cathodic current: 2~3 A/dm$^2$; Room temperature; Time: 1 min. |
| 7. Electroless plating Ni—P | NiCl$_2$.6H$_2$O: 20~30 g/l; Na$_3$C$_6$H$_5$O$_7$.6H$_2$O: 15~30 g/l; NaH$_2$PO$_2$: 15~35 g/l; C$_3$H$_6$O$_3$: 20~30 g/l; Temperature: 85~90° C.; pH: 4.6~5.0 |
| 8. Rinsing | With water. Room temperature. |
| 9. Electroless plating with Ni—Cu—P-PTFE | 85~90° C., pH: 4.8~5.0 |
| 10. Rinsing | With water. Room temperature. |

The invention claimed is:

1. A modified surface wherein the adhesion or attachment of cells, proteins and/or prions to the modified surface has been minimised or prevented by adjusting the Lifshitz-van der Waals (LW) surface free energy of an unmodified surface to be equal to or approximately equal to the Lifshitz-van der Waals (LW) surface free energy of the cells, proteins and/or prions in a solution and/or whole blood surrounding the surface,
   wherein the surface is modified with a coating of modified diamond-like carbon (DLC),
   wherein the coated surface inhibits bacterial adhesion and colonisation, thrombus adhesion to the surface and foulant formation,
   wherein the surface is one which comes into contact with cells, proteins and/or prions within a living human or animal body,
   wherein the LW surface free energy of the modified surface is in a range of about 25 mN/m to about 45 mN/m, and
   wherein the adhesion or attachment of said cells, proteins and/or prions is minimised or prevented by modifying the surface free energy $\gamma^{LW}_{surface}$ of the surface in accordance with the Lifshitz-van der Waals (LW) surface free energy of the cells, proteins and/or prions so that:

$$\gamma^{LW}_{surface} \approx \gamma^{LW}_{S,Min}$$

wherein $\gamma^{LW}_{S,Min}$ is the minimum level of attachment to a surface S and is defined as follows:

$$\sqrt{\gamma^{LW}_{S,Min}} = (1/2)(\sqrt{\gamma^{LW}_{cells\,and/or\,proteins\,and/or\,prions}} + \sqrt{\gamma^{LW}_{solution\,and/or\,whole\,blood}})$$

where $\gamma^{LW}_{cells,\,proteins\,and/or\,prions}$ is the LW surface free energy of the cells, proteins and/or prions, and $\gamma^{LW}_{solution\,and/or\,whole\,blood}$ is the LW surface free energy of the solution and/or of whole blood.

2. A modified surface according to claim 1 wherein the surface is modified with a coating of diamond-like carbon (DLC) which is modified by incorporating elements selected from any of the following: halogens; Group IV elements; Group V elements;
   Group VI elements; and transition metals.

3. A modified surface according to claim 2 wherein the elements are present in an amount of 0-40% by weight.

4. A modified surface according to claim 2 wherein the elements incorporated into the diamond-like carbon by co-sputtering.

5. A modified surface according to claim 2 wherein the elements are incorporated into the diamond-like carbon (DLC) using reactive gases, silicon organic monomers, gaseous hydrocarbons, O$_2$, and/or N$_2$.

6. A modified surface according to claim 1 wherein the modified diamond-like carbon (DLC) is deposited using any of the following methods: microwave plasma deposition, plasma-enhanced vapour deposition, plasma-induced cold deposition, magnetron sputtering and ion beam-assisted deposition.

7. A modified surface according to claim 1 wherein the modified surface is part of a medical device.

8. A modified surface according to claim 7 wherein the medical device is selected from any of the following: endoscopes and accessories; ophthalmic equipment; dental equipment; surgical instruments; heart valves; stents; catheters; joint prostheses; intraocular lenses, dental implants, electrodes and cable equipment.

9. A modified surface according to claim 1 wherein the modified surface inhibits the following bacteria: *Staphylococcus epidermidis, Staphylococcus aureus, Psuedomonas aeruginosa, Escherichia coli, Candida albicans* or any other microorganisms which could cause device-related infections.

10. A device comprising a modified surface according to claim 1.

* * * * *

UNITED STATES PATENT AND TRADEMARK OFFICE
CERTIFICATE OF CORRECTION

PATENT NO. : 8,247,064 B2
APPLICATION NO. : 10/524755
DATED : August 21, 2012
INVENTOR(S) : Zhao et al.

It is certified that error appears in the above-identified patent and that said Letters Patent is hereby corrected as shown below:

Column 10, Claim 1, Line 21: Please correct "$\gamma^{LW}_{surface} \approx \gamma^{LW}_{S,Min}$"
to read -- $\gamma^{LW}_{surface} \approx \gamma^{LW}_{S,Min}$ --

Claim 2, Lines 35-36: Please combine the lines so that it reads:
-- Group V elements; Group VI elements; and transition metals. --

Signed and Sealed this
Fifth Day of February, 2013

Teresa Stanek Rea
*Acting Director of the United States Patent and Trademark Office*